United States Patent
Carlini

(10) Patent No.: US 7,503,973 B1
(45) Date of Patent: Mar. 17, 2009

(54) NANOSIZED PARTICLES OF BENZIMIDAZOLONE PIGMENTS

(75) Inventor: Rina Carlini, Oakville (CA)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 12/044,613

(22) Filed: Mar. 7, 2008

(51) Int. Cl.
*C09B 67/20* (2006.01)
*C09D 11/00* (2006.01)
*C09D 11/02* (2006.01)
*C07D 235/00* (2006.01)
*C07D 235/02* (2006.01)

(52) U.S. Cl. ............... 106/496; 106/31.77; 106/31.78; 106/31.79; 106/498; 430/108.23; 548/301.7; 548/302.7; 548/304.4; 548/305.4

(58) Field of Classification Search ............ 106/31.77, 106/31.78, 31.79, 496, 498; 548/301.7, 302.7, 548/304.4, 305.4; 430/108.23
See application file for complete search history.

(56) References Cited

U.S. PATENT DOCUMENTS

| | | | |
|---|---|---|---|
| 5,278,020 A | 1/1994 | Grushkin et al. | |
| 5,290,654 A | 3/1994 | Sacripante et al. | |
| 5,308,734 A | 5/1994 | Sacripante et al. | |
| 5,344,738 A | 9/1994 | Kmiecik-Lawrynowicz et al. | |
| 5,346,797 A | 9/1994 | Kmiecik-Lawrynowicz et al. | |
| 5,364,729 A | 11/1994 | Kmiecik-Lawrynowicz et al. | |
| 5,370,963 A | 12/1994 | Patel et al. | |
| 5,403,693 A | 4/1995 | Patel et al. | |
| 5,418,108 A | 5/1995 | Kmiecik-Lawrynowicz et al. | |
| 5,679,138 A | 10/1997 | Bishop et al. | |
| 6,706,864 B1 * | 3/2004 | Vincent et al. | 534/774 |
| 7,371,870 B2 * | 5/2008 | Hosaka et al. | 548/305.4 |
| 2005/0109240 A1 | 5/2005 | Maeta et al. | |
| 2006/0063873 A1 | 3/2006 | Lin et al. | |
| 2007/0012221 A1 | 1/2007 | Maeta et al. | |

FOREIGN PATENT DOCUMENTS

| | | | |
|---|---|---|---|
| JP | 2003-082256 A | * | 3/2003 |
| WO | 2006/005536 | | 1/2006 |
| WO | 2006/132443 | | 12/2006 |

OTHER PUBLICATIONS

U.S Appl. No. 11/759,906 to Maria Birau et al. filed Jun. 7, 2007.
U.S. Appl. No. 11/759,913 to Rina Carlini et al. filed Jun. 7, 2007.
Hideki Maeta et al., "New Synthetic Method of Organic Pigment Nano Particle by Micro Reactor System," http://aiche.confex.com/aiche/s06/preliminaryprogram/abstract_40072.htm (date unknown).
K. Balakrishnan et al., "Effect of Side-Chain Substituents on Self-Assembly of Perylene Diimide Molecules: Morphology Control," *J. Am. Chem. Soc.*, vol. 128, p. 7390-98 (2006), no month.
E.F. Paulus, "Molecular and crystal structure of C.I. Pigment Red 208, 12514, n-butyl-2-[2-oxo-3-[N-(2-oxo-2,3-dihydro-5-benzimidazolyl)-carbamoyl]-naphthylidenhydrazino]-benzoat (PV-Rot HF2B),"; Zeitschrift fur *Kristallographie*, vol. 160, pp. 235-243 (1982), no month.
K. Hunger et al., "Uber die Molekul- und Kristallstruktur gelber Mono-"azo"-Pigmente," *Farbe+Lack*, vol. 88, pp. 453-458 (1982), no month.

* cited by examiner

*Primary Examiner*—Anthony J Green
(74) *Attorney, Agent, or Firm*—Oliff & Berridge, PLC

(57) ABSTRACT

A nanoscale pigment particle composition includes an organic benzimidazolone pigment, and a sterically bulky stabilizer compound, wherein the benzimidazolone pigment associates non-covalently with the sterically bulky stabilizer compound; and the presence of the associated stabilizer limits the extent of particle growth and aggregation, to afford nanoscale-sized pigment particles.

25 Claims, No Drawings

NANOSIZED PARTICLES OF BENZIMIDAZOLONE PIGMENTS

TECHNICAL FIELD

This disclosure is generally directed to nanoscale benzimidazolone pigment particle compositions, and methods for producing such compositions. More specifically, this disclosure is directed to nanoscale pigment particle compositions comprising benzimidazolone molecules associated with a sterically bulky stabilizer compound, and methods for producing such compositions. Such particles are useful, for example, as nanoscopic colorants for such compositions as inks, toners and the like.

CROSS-REFERENCE TO RELATED APPLICATIONS

Disclosed in commonly assigned U.S. patent application Ser. No. 11/759,913 to Rina Carlini et al. filed Jun. 7, 2007, is a nanoscale pigment particle composition, comprising: an organic monoazo laked pigment including at least one functional moiety, and a sterically bulky stabilizer compound including at least one functional group, wherein the functional moiety associates non-covalently with the functional group; and the presence of the associated stabilizer limits the extent of particle growth and aggregation, to afford nanoscale-sized pigment particles. Also disclosed is a process for preparing nanoscale-sized monoazo laked pigment particles, comprising: preparing a first reaction mixture comprising: (a) a diazonium salt including at least one functional moiety as a first precursor to the laked pigment and (b) a liquid medium containing diazotizing agents generated in situ from nitrous acid derivatives; and preparing a second reaction mixture comprising: (a) a coupling agent including at least one functional moiety as a second precursor to the laked pigment and (b) a sterically bulky stabilizer compound having one or more functional groups that associate non-covalently with the pigment; and (c) a liquid medium combining the first reaction mixture into the second reaction mixture to form a third solution and effecting a direct coupling reaction which forms a monoazo laked pigment composition having nanoscale particle size and wherein the functional moiety on the pigment associates non-covalently with the functional group on the steric stabilizer. Further disclosed is a process for preparing nanoscale monoazo laked pigment particles, comprising: providing a monoazo precursor dye to the monoazo laked pigment that includes at least one functional moiety; subjecting the monoazo precursor dye to an ion exchange reaction with a cation salt in the presence of a sterically bulky stabilizer compound having one or more functional groups; and precipitating the monoazo laked pigment as nanoscale particles, wherein the functional moiety of the pigment associates non-covalently with the functional group of the stabilizer.

Disclosed in commonly assigned U.S. patent application Ser. No. 11/759,906 to Maria Birau et al. filed Jun. 7, 2007, is a nanoscale pigment particle composition, comprising: a quinacridone pigment including at least one functional moiety, and a sterically bulky stabilizer compound including at least one functional group, wherein the functional moiety associates non-covalently with the functional group; and the presence of the associated stabilizer limits the extent of particle growth and aggregation, to afford nanoscale-sized particles. Also disclosed is a process for preparing nanoscale quinacridone pigment particles, comprising: preparing a first solution comprising: (a) a crude quinacridone pigment including at least one functional moiety and (b) a liquid medium; preparing a second solution comprising: (a) a sterically bulky stabilizer compound having one or more functional groups that associate non-covalently with the functional moiety, and (b) a liquid medium; combining the first solution into the second solution to form a third solution and effecting a reconstitution process which forms a quinacridone pigment composition wherein the functional moiety of the pigment associates non-covalently with the functional group of the stabilizer and having nanoscale particle size. Still further is disclosed a process for preparing nanoscale quinacridone pigment particles, comprising: preparing a first solution comprising a quinacridone pigment including at least one functional moiety in an acid; preparing a second solution comprising an organic medium and a sterically bulky stabilizer compound having one or more functional groups that associate non-covalently with the functional moiety of the pigment; treating the second solution containing with the first solution; and precipitating quinacridone pigment particles from the first solution, wherein the functional moiety associates non-covalently with the functional group and the quinacridone pigment particles have a nanoscale particle size.

The entire disclosures of the above-mentioned applications are totally incorporated herein by reference.

BACKGROUND

A printing ink is generally formulated according to strict performance requirements demanded by the intended market application and required properties. Whether formulated for office printing or for production printing, a particular ink is expected to produce images that are robust and durable under stress conditions. In a typical design of a piezoelectric ink jet printing device, the image is applied by jetting appropriately colored inks during four to six rotations (incremental movements) of a substrate (an image receiving member or intermediate transfer member) with respect to the ink jetting head, i.e., there is a small translation of the printhead with respect to the substrate in between each rotation. This approach simplifies the printhead design, and the small movements ensure good droplet registration. At the jet operating temperature, droplets of liquid ink are ejected from the printing device and, when the ink droplets contact the surface of the recording substrate, either directly or via an intermediate heated transfer belt or drum, they quickly solidify to form a predetermined pattern of solidified ink drops.

Pigments are a type of insoluble colorant that are useful in a variety of applications such as, for example, paints, plastics and inks, including inkjet printing inks. Dyes on the other hand, are readily soluble colorants and have typically been the colorants of choice for applications such as inkjet printing inks. Dyes have also offered superior and brilliant color quality with an expansive color gamut for inks, when compared to conventional pigments. However, since dyes are molecularly dissolved in the ink vehicle, they are often susceptible to unwanted interactions that lead to poor ink performance, for example photo-oxidation from light (leads to poor lightfastness), dye diffusion from the ink into paper or other substrates (leads to poor image quality and showthrough), and the ability for the dye to leach into another solvent that makes contact with the image (leads to poor water-/solvent-fastness). In certain situations, pigments have the potential to be a better alternative as colorants for inkjet printing inks since they are insoluble and cannot be molecularly dissolved within the ink matrix, and in most cases do not experience colorant diffusion or color degradation. Pigments can also be significantly less expensive than dyes, and so are attractive colorants for use in all printing inks.

Key challenges with using pigments for inkjet inks are their large particle sizes and wide particle size distribution, the combination of which can pose critical problems with reliable jetting of the ink (i.e. inkjet nozzles are easily blocked). Pigments are rarely obtained in the form of single crystal nanoparticles, but rather as micron-sized large aggregates of crystals and often having a wide distribution of aggregate sizes. The color characteristics of the pigment aggregate can vary widely depending on the aggregate size and crystal morphology. Thus, an ideal colorant that is widely applicable in, for example, inks and toners, is one that possesses the best properties of both dyes and pigments, namely: 1) superior coloristic properties (large color gamut, brilliance, hues, vivid color); 2) color stability and durability (thermal, light, chemical and air-stable colorants); 3) minimal or no colorant migration; 4) processable colorants (easy to disperse and stabilize in a matrix); and 5) inexpensive material cost. Thus, there is a need addressed by embodiments of the present invention, for smaller nano-sized pigment particles that minimize or avoid the problems associated with conventional larger-sized pigment particles. There further remains a need for processes for making and using such improved nano-sized pigment particles as colorant materials. The present nano-sized pigment particles are useful in, for example, paints, coatings and inks (e.g., inkjet printing inks) and other compositions where pigments can be used such as plastics, optoelectronic imaging components, photographic components, and cosmetics among others.

The following documents provide background information:

Hideki Maeta et al., "New Synthetic Method of Organic Pigment Nano Particle by Micro Reactor System," in an abstract available on the internet describes a new synthetic method of an organic pigment nanoparticle was realized by micro reactor. A flowing solution of an organic pigment, which dissolved in an alkaline aqueous organic solvent, mixed with a precipitation medium in a micro channel. Two types of micro reactor can be applied efficiently on this build-up procedure without blockage of the channel. The clear dispersion was extremely stable and had narrow size distribution, which were the features, difficult to realize by the conventional pulverizing method (breakdown procedure). These results proved the effectiveness of this process on micro reactor system.

U.S. Patent Application Publication No. 2005/0109240 describes a method of producing a fine particle of an organic pigment, containing the steps of: flowing a solution of an organic pigment dissolved in an alkaline or acidic aqueous medium, through a channel which provides a laminar flow; and changing a pH of the solution in the course of the laminar flow.

WO 2006/132443 A1 describes a method of producing organic pigment fine particles by allowing two or more solutions, at least one of which is an organic pigment solution in which an organic pigment is dissolved, to flow through a microchannel, the organic pigment solution flows through the microchannel in a non-laminar state. Accordingly, the contact area of solutions per unit time can be increased and the length of diffusion mixing can be shortened, and thus instantaneous mixing of solutions becomes possible. As a result, nanometer-scale monodisperse organic pigment fine particles can be produced in a stable manner.

K. Balakrishnan et al., "Effect of Side-Chain Substituents on Self-Assembly of Perylene Diimide Molecules: Morphology Control," *J. Am. Chem. Soc.*, vol. 128, p. 7390-98 (2006) describes the use of covalently-linked aliphatic side-chain substituents that were functionalized onto perylene diimide molecules so as to modulate the self-assembly of molecules and generate distinct nanoparticle morphologies (nano-belts to nano-spheres), which in turn impacted the electronic properties of the material. The side-chain substituents studied were linear dodecyl chain, and a long branched nonyldecyl chain, the latter substituent leading to the more compact, spherical nanoparticle.

U.S. Patent Application Publication No. 2006/0063873 discloses a process for preparing nano water paint comprising the steps of: A. modifying the chemical property on the surface of nano particles by hydroxylation for forming hydroxyl groups at high density on the surface of the nano particles; B. forming self-assembly monolayers of low surface energy compounds on the nano particles by substituting the self-assembly monolayers for the hydroxyl groups on the nano particles for disintegrating the clusters of nano particles and for forming the self-assembly monolayers homogeneously on the surface of the nano particles; and C. blending or mixing the nano particles having self-assembly monolayers formed thereon with organic paint to form nano water paint.

WO 2006/005536 discloses a method for producing nanoparticles, in particular, pigment particles. Said method consists of the following steps: (i) a raw substance is passed into the gas phase, (ii) particles are produced by cooling or reacting the gaseous raw substance and (iii) an electrical charge is applied to the particles during the production of the particles in step (ii), in a device for producing nanoparticles. The disclosure further relates to a device for producing nanoparticles, comprising a supply line, which is used to transport the gas flow into the device, a particle producing and charging area in order to produce and charge nanoparticles at essentially the same time, and an evacuation line which is used to transport the charged nanoparticles from the particle producing and charging area.

U.S. Pat. No. 5,679,138 discloses a process for making ink jet inks, comprising the steps of: (A) providing an organic pigment dispersion containing a pigment, a carrier for the pigment and a dispersant; (B) mixing the pigment dispersion with rigid milling media having an average particle size less than 100 μm; (C) introducing the mixture of step (B) into a high speed mill; (D) milling the mixture from step (C) until a pigment particle size distribution is obtained wherein 90% by weight of the pigment particles have a size less than 100 nanometers (nm); (E) separating the milling media from the mixture milled in step (D); and (F) diluting the mixture from step (E) to obtain an ink jet ink having a pigment concentration suitable for ink jet printers.

U.S. Patent Application Publication No. 2007/0012221 describes a method of producing an organic pigment dispersion liquid, which has the steps of: providing an alkaline or acidic solution with an organic pigment dissolved therein and an aqueous medium, wherein a polymerizable compound is contained in at least one of the organic pigment solution and the aqueous medium; mixing the organic pigment solution and the aqueous medium; and thereby forming the pigment as fine particles; then polymerizing the polymerizable compound to form a polymer immobile from the pigment fine particles.

The appropriate components and process aspects of each of the foregoing may be selected for the present disclosure in embodiments thereof, and the entire disclosure of the above-mentioned references are totally incorporated herein by reference.

SUMMARY

The present disclosure addresses these and other needs, by providing nanoscale benzimidazolone pigment particle compositions, and methods for producing such compositions.

In an embodiment, the present disclosure provides a nanoscale pigment particle composition, comprising:
  a benzimidazolone pigment, and
  a sterically bulky stabilizer compound associated non-covalently with the benzimidazolone pigment;
  wherein the presence of the associated stabilizer limits an extent of particle growth and aggregation, to afford nanoscale-sized pigment particles.

In another embodiment, the present disclosure provides a process for preparing nanoscale particles of benzimidazolone pigments, comprising:

providing one or more organic pigment precursors to a benzimidazolone pigment, providing a solution or suspension of a sterically bulky stabilizer compound that associates non-covalently with the benzimidazolone pigment, and carrying out a chemical reaction to form a benzimidazolone pigment composition, whereby the pigment precursors are incorporated within the benzimidazolone pigment and one or more functional moieties on the benzimidazolone pigment is non-covalently associated with the stabilizer, so as to limit the extent of particle growth and aggregation and result in nanoscale-sized pigment particles.

DETAILED DESCRIPTION OF EXEMPLARY EMBODIMENTS

Embodiments of the present disclosure provide nanoscale benzimidazolone pigment particle compositions and methods for producing such nanoscale benzimidazolone pigment particle compositions. The nanoscale pigment particle compositions generally comprise an organic benzimidazolone pigment including at least one functional moiety that associates non-covalently with a functional group from a sterically bulky stabilizer compound. The presence of the associated sterically bulky stabilizer limits the extent of particle growth and aggregation, to afford nanoscale particles.

Benzimidazolone pigments in this disclosure are of the azo-benzimidazolone class of organic pigments, which are generally derived from a substituted aromatic amine as the diazo precursor and a coupling agent that contains a benzimidazolone functional moiety. Azo-benzimidazolone pigments are known to provide colors with hues ranging from yellow to red to brownish-red, depending primarily upon the chemical composition of the coupling component.

The structure of azo-benzimidazolone pigments disclosed herein can be represented with the general structure in Formula 1, comprised of a diazo component group (denoted $G_{DC}$) and a nucleophilic coupling component group (denoted as $G_{CC}$) that are linked together with one azo group (N=N). Either or both of the diazo and coupling groups can contain within their structures the benzimidazolone functional moiety shown in Formula 2, wherein the substituents $R_x$, $R_y$, and $R_z$ are most typically hydrogen and halogen, but can also include small aliphatic group of less than 6 carbon atoms, small arene or heterocyclic arene group of less than 10 carbon atoms, or derivatives of carbonyl compounds such as aldehydes, ketones, ester, acids, anhydrides, urethanes, ureas, thiol esters, thioesters, xanthates, isocyanates, thiocyanates, or any combination of these substituents.

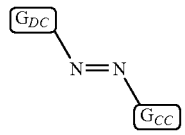

Formula 1

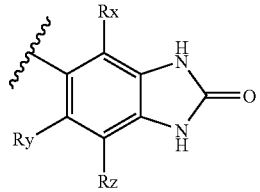

Formula 2

The diazo group ($G_{DC}$) can be derived from a variety of substituted aniline or naphthylamine compounds, and while they can have many possible structures, the pigment compositions of this disclosure include the diazo group compositions $DC_1$ to $DC_5$ shown below:

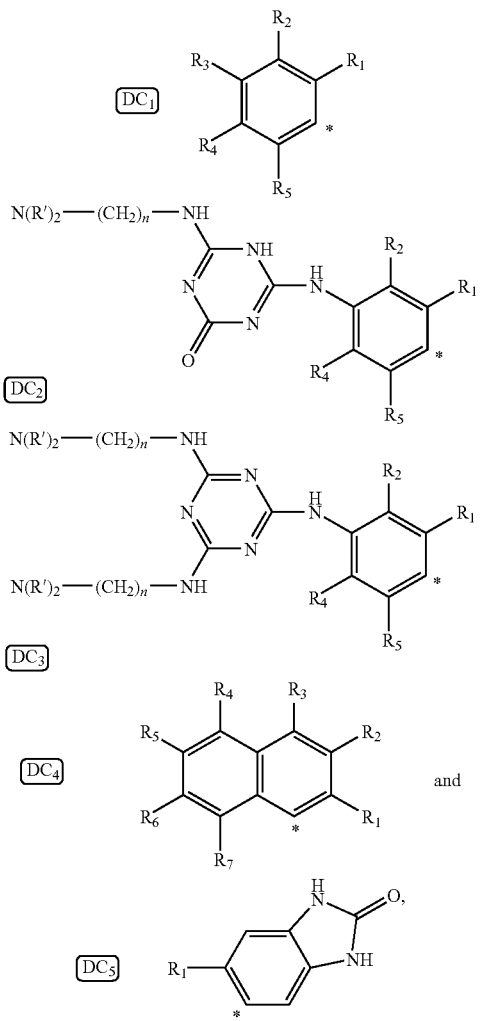

In such structures, the asterisk (*) indicates the point of attachment to the amino group (—$NH_2$) in the pigment precursor structure, and also the point of attachment to the azo functional group (—N=N—) in the pigment structure. $R_1$ to $R_7$ independently represent H; $CH_3$; $CO_2H$; $CO_2CH_3$; $CO_2(CH_2)_nCH_3$ wherein n=0-5; $CONH_2$; $(CO)R_aR_b$ wherein $R_a$, $R_b$ can independently represent H, $C_6H_5$, $(CH_2)_nCH_3$ wherein n=0-12, or they can represent $(CH_2)_nN(CH_3)_2$ wherein n=1-

5; OCH$_3$; OCH$_2$CH$_2$OH; NO$_2$; SO$_3$H; Cl; Br; I; F; or any of the following structural groups:

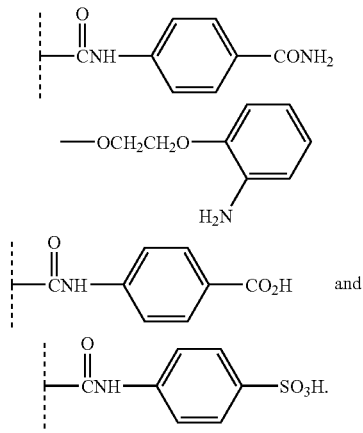

In DC$_2$ and DC$_3$ R' represents H, (CH$_2$)$_n$CH$_3$, or C$_6$H$_5$, and n represents a number of from 1 to about 6. In some instances, the diazo group precursor can be a substituted aniline compound that possesses the benzimidazolone functional moiety of Formula 2, as for example in the structure of DC$_5$.

The coupling component group (G$_{CC}$) most typically contains the benzimidazolone functional group (Formula 2) and generally consists of an amide of 5-aminobenzimidazolone. There are two common classes of amides used as the coupling component when making azo-benzimidazolone pigments, acetoacetamides of 5-aminobenzimidazolones (denoted as CC 1) and 3-hydroxy-2-naphthamides of 5-aminobenzimidazolones (denoted as CC 2):

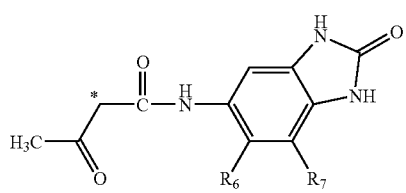

CC1:

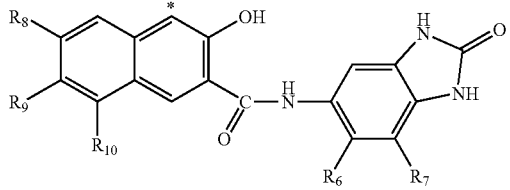

CC2:

In such structures, the asterisk (*) indicates the point of attachment to the azo functional group (—N═N—) in the pigment structure, and R$_6$, R$_7$, R$_8$, R$_9$, and R$_{10}$ are independently H, Br, Cl, I, F, or CH$_3$. It is known that the structure of the coupling component for these pigments will determine the range of colors produced by the pigment. For instance, azo-benzimidazolone pigments produced with coupling components that have general structure CC 1 will exhibit yellow to orange hues, whereas use of coupling components having the general structure CC 2 will exhibit red to brown (or maroon) hues.

As with many azo class colorants that produce yellow or red or brown hues, the structure of the azo-benzimidazolone pigments can adopt more than one tautomeric form due to the presence of strong intra-molecular hydrogen bonding between the N atoms of the azo group and the H atom of a nearby heteroatom substituent on the coupling component group G$_{CC}$. For example, the composition of Pigment Red 208 (Color Index No. 12514) shown in Formula 3 depicts the extensive intra-molecular hydrogen bonding with the hashed bond lines in both the "azo" tautomer (3a) and the "hydrazone" tautomer (3b). It is also understood that the general structure in Formula (I) is understood to denote both such tautomeric structural forms.

Formula 3

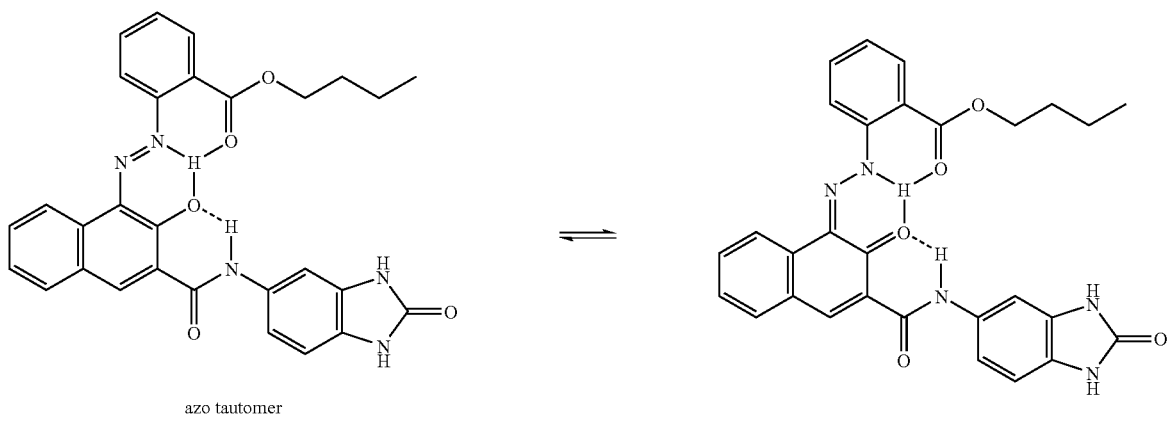

Pigment Red 208 (C.I. No. 12514)

In addition to the presence of intra-molecular hydrogen bonding, it is also known that azo-benzimidazolone pigments are capable of forming one-dimensional, extended network structures due to strong inter-molecular hydrogen bonding. Evidence has been found in the X-ray diffraction patterns of such pigments, where the large intermolecular spacings have suggested that pairs of pigment molecules associate strongly together (via inter-molecular H bonds) to form a microstructure of one-dimensional bands. See, for example, K. Hunger, E. F. Paulus, D. Weber; *Farbe+Lack*; (1982), 88, 453, and E. F. Paulus; *Kristallogr.* (1982), 160, 235, the entire disclosures of which are incorporated herein by reference. Formula 4 illustrates the one-dimensional network consisting of inter-molecular hydrogen bonds for Pigment Red 208;

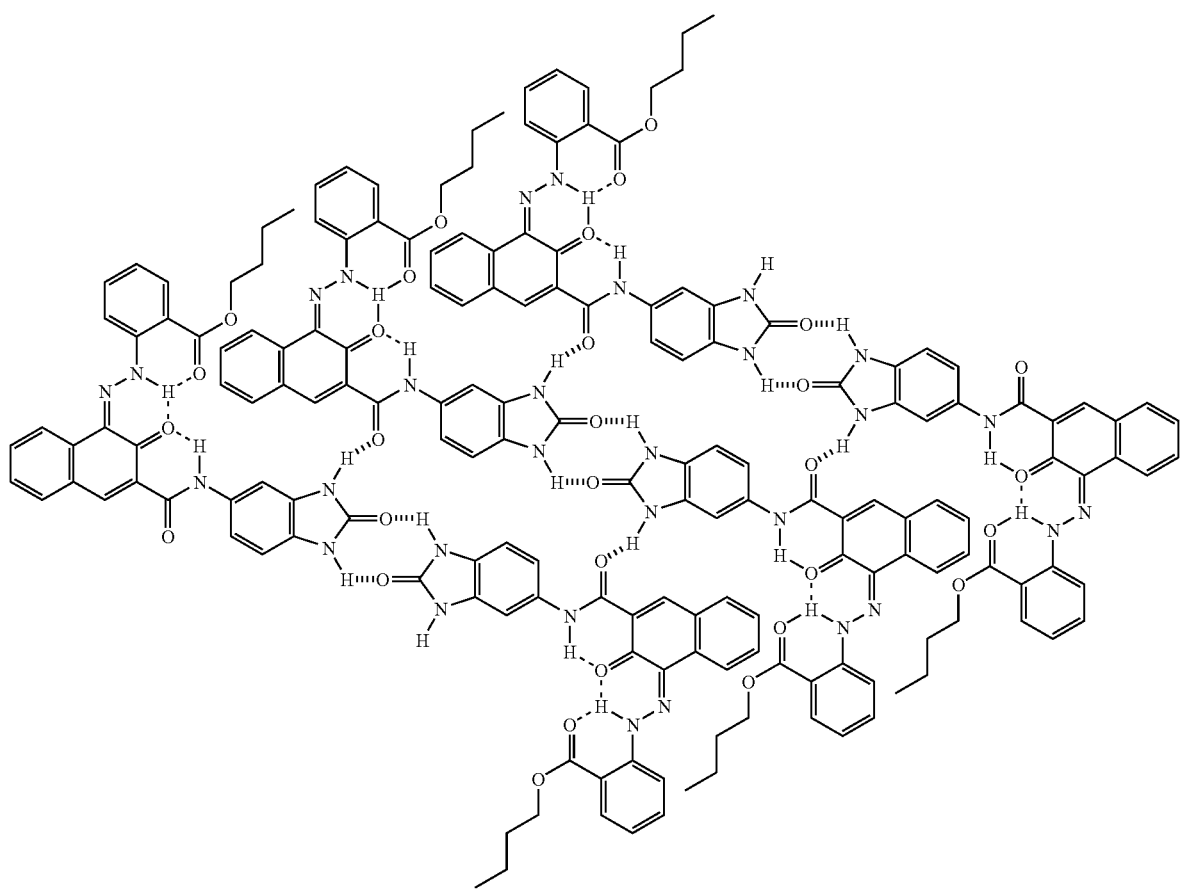

Formula 4

Furthermore, the existence of these reinforcing intra- and inter-molecular hydrogen bonds provide enhanced performance properties for the azo-benzimidazolone pigments, such as high thermal stability, high lightfastness, high color-migration resistance and high solvent fastness. The functional moiety in such pigments that is a key structural element of the inter-molecular hydrogen bonds, and helps to provide the enhanced robustness properties described above, is the benzimidazolone group as shown in Formula 2. Given the propensity of this moiety to readily partake in single-point and double-point hydrogen bonding, it is conceivable that another compound having either the same or different functional moiety, is capable of associating non-covalently, such as through inter-molecular hydrogen bonds, with azo-benzimidazolone pigments and will therefore have a high binding affinity for such pigments. Such compounds are included in a group of compounds which herein are referred to as "stabilizers", and that function to reduce the surface tension of the pigment particle and neutralize attractive forces between two or more pigment particles or structures, thereby stabilizing the chemical and physical structure of the pigment. In addition to the functional moiety having high pigment affinity (referred to hereafter as "pigment-affinic" functional moiety), these stabilizer compounds can also possess one or more hydrophobic groups, such as long alkyl hydrocarbon groups, or alkyl-aryl hydrocarbon groups, wherein the alkyl groups can be linear, cyclic or branched in structure and have at least 6 or more carbons in total. The presence of the additional hydrophobic groups in such stabilizers can serve several functions: (1) to compatibilize the pigment for better dispersability in the targeted vehicle or matrix; and (2) to provide a sterically bulky layer surrounding the pigment particle, thereby preventing or limiting the approach of other pigment particles or molecules that results in uncontrolled aggregation, and ultimately particle growth. Such compounds having both a pigment-affinic functional moiety that associates noncovalently with the pigment, as well as one or more sterically bulky hydrocarbon groups that provide a surface barrier to other pigment particles, are referred to as "steric stabilizers" and have been used in various ways to alter the surface characteristics of conventional pigments and other particles requiring stabilization (for example, latex particles in paints, metal oxide nanoparticles in anti-scratch coatings, among others).

The term "precursor" as used in "precursor to the benzimidazolone pigment" can be any chemical substance that is an advanced intermediate in the total synthesis of a compound (such as the benzimidazolone pigment). In embodiments, the precursor to the azo-benzimidazolone pigment may or may not be a colored compound. In embodiments, where the azo-benzimidazolone pigment and the precursor have a structural moiety or characteristic in common, the phrase "benzimidazolone pigment/pigment precursor" is used for convenience rather than repeating the same discussion for each of the pigment and the pigment precursor.

The benzimidazolone pigment/precursor in embodiments can form one or more hydrogen bonds with selected stabilizer compounds, per benzimidazolone unit or molecule. For example, in embodiments, the benzimidazolone pigment/precursor can form one, two, three, four, or more hydrogen bonds with selected stabilizer compounds, per benzimidazolone. Thus, for example in the benzimidazolone functional moiety of Formula 2, a hydrogen atom from the —NH group and/or an oxygen atom in the carbonyl (C═O) group can form hydrogen bonds with complementary oxygen, nitrogen and/or hydrogen atoms located on selected stabilizer compounds. In the same way, the two hydrogen atoms from the —NH group in the benzimidazolone unit can form two separated hydrogen bonds with complementary oxygen or nitrogen atoms found on the stabilizer. Of course, other combinations are also possible and encompassed herein.

The stabilizer can be any compound that has the function of limiting the self-assembly of colorant molecules during pigment synthesis, and/or limiting the extent of aggregation of primary pigment particles, so as to produce predominantly nanoscale-sized pigment particles. The stabilizer compound should have a hydrocarbon moiety that provides sufficient steric bulk to enable the function of the stabilizer to regulate pigment particle size. The hydrocarbon moiety in embodiments is predominantly aliphatic, but in other embodiments can also incorporate aromatic groups, and generally contains at least 6 carbon atoms, such as at least 12 carbons or at least 16 carbons, and not more than about 100 carbons, but the actual number of carbons can be outside of these ranges. The hydrocarbon moiety can be either linear, cyclic or branched, and in embodiments is desirably branched, and may or may not contain cyclic moieties such as cycloalkyl rings or aromatic rings. The aliphatic branches are long with at least 2 carbons in each branch, such as at least 6 carbons in each branch, and not more than about 100 carbons.

It is understood that the term "steric bulk" is a relative term, based on comparison with the size of the pigment or pigment precursor to which it becomes non-covalently associated. In embodiments, the phrase "steric bulk" refers to the situation when the hydrocarbon moiety of the stabilizer compound that is hydrogen bonded to the pigment/precursor surface, occupies a 3-dimensional spatial volume that effectively prevents the approach or association of other chemical entities (e.g. colorant molecules, primary pigment particles or small pigment aggregate) toward the pigment/precursor surface. Thus, the stabilizer should have its hydrocarbon moiety large enough so that as several stabilizer molecules become non-covalently associated (for example, by hydrogen bonding, van der Waals forces, aromatic pi-pi interactions, or other) with the pigment/pigment precursor, the stabilizer molecules act as surface barrier agents for the primary pigment particles and effectively shields them, thereby limiting the growth of the pigment particles and affording only nanoparticles of the pigment. For example, for the benzimidazolone pigments Pigment Red 175 and Pigment Yellow 151, the following stabilizer structures are considered to have adequate "steric bulk" so as to enable the stabilizer to limit the extent of pigment self-assembly or aggregation and mainly produce pigment nano-sized particles:

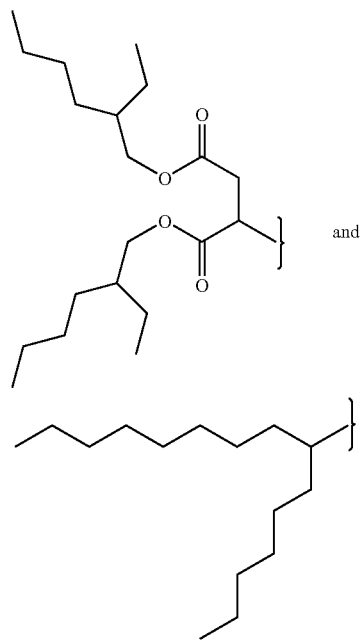

Suitable stabilizer compounds are those that have a hydrophilic or a polar functional group with available heteroatoms for hydrogen bonding with the pigment/pigment precursor, as well as a non-polar or hydrophobic sterically bulky group that has at least 6 carbons and not more than 50 carbons and is predominantly aliphatic (or fully saturated) but can include some ethylenically unsaturated groups and/or aryl groups. Classes of suitable stabilizer compounds include the following: the mono- and di-carboxylic acids, mono- and di-esters, and mono- and di-primary amide derivatives of pyridine, piperidine, piperazine, morpholine and pyrroles; monosubstituted pyridine, piperazine, piperidine, morpholine, pyrrole, imidazole, thiazole and their cationic salts, wherein the substituent is a long-chain or branched aliphatic hydrocarbon; poly(vinyl pyrrolidone) and copolymers of poly(vinyl pyrrolidone) with α-olefins or other ethylenically unsaturated monomer compounds, such as for example poly(vinyl pyrrolidone-graft-1-hexadecane) and poly(vinyl pyrrolidone-co-eicosene) and the like; poly(vinyl imidazole) and copolymers of poly(vinyl imidazole) with α-olefins or other ethylenically unsaturated monomer compounds; poly(vinyl pyridine) and copolymers of poly(vinyl pyridine) with α-olefins or styrene, or other ethylenically unsaturated monomer compounds; long-chain or branched aliphatic primary amides and amidines, including Guerbet-type primary amides and amidines; semicarbazides and hydrazones of long-chain aliphatic and/or branched aldehydes and ketones; mono-substituted ureas and N-alkyl-N-methyl ureas, wherein the substituent is a long-chain or branched aliphatic hydrocarbon; mono-substituted monosubstituted guanidines and guanidinium salts, wherein the substituent is a long-chain or branched aliphatic hydrocarbon; mono- and di-substituted succinimides, such as 2-alkyl- and 2,3-dialkyl-succinimides, and mono- and di-substituted succinic acids or their esters, wherein one or more alkyl substituent is comprised of a long-chain or branched aliphatic hydrocarbon having between 6 and 50 carbon atoms; mixtures thereof; and the like.
Representative examples of such suitable stabilizer compounds include (but are not limited to) the following compounds:
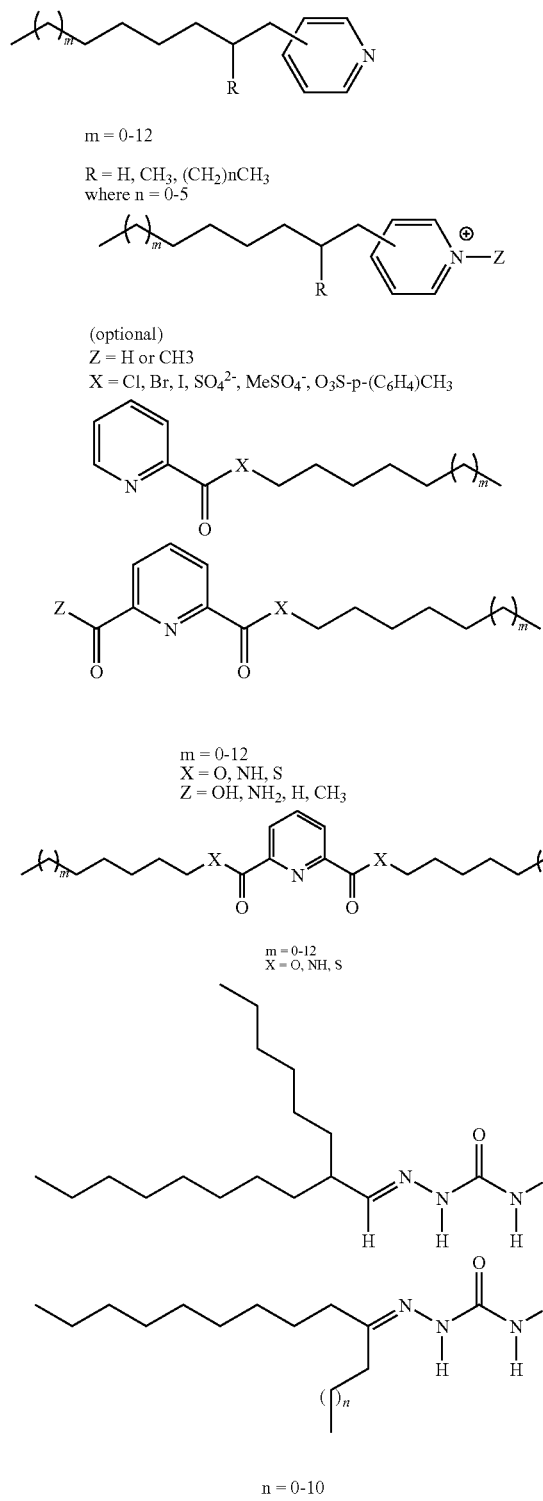
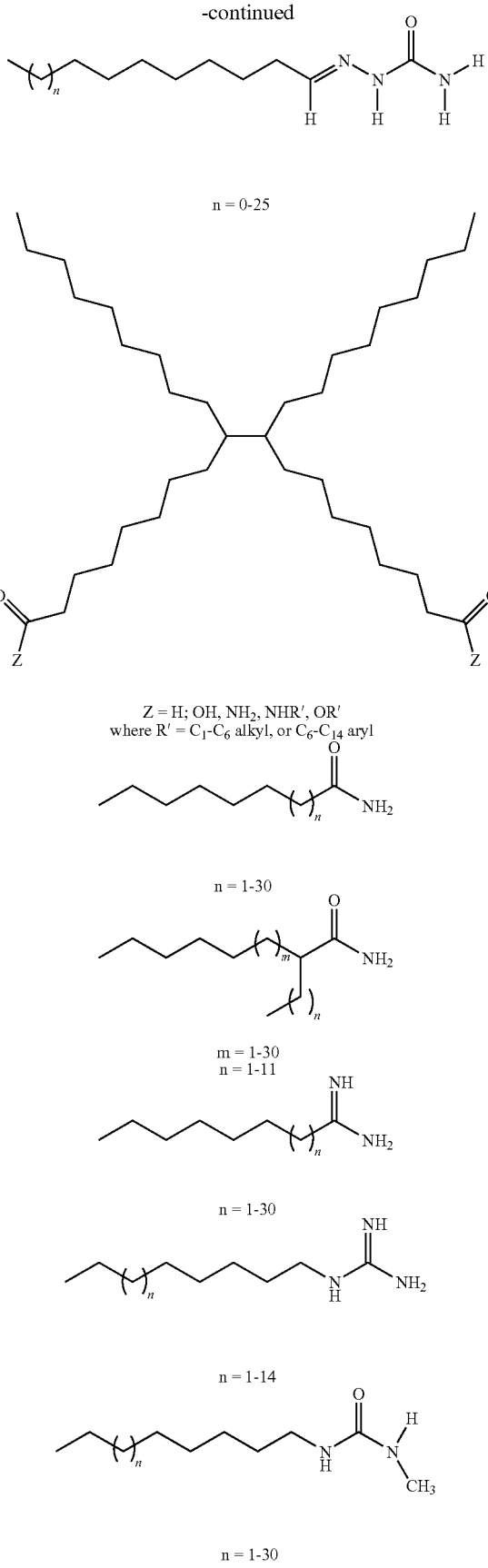

In additional embodiments, other stabilizer compounds having different structures than those described previously may be used in addition to sterically bulky stabilizer compounds, to function as surface active agents (or surfactants) that either prevent or limit the degree of pigment particle aggregation. Representative examples of such surface active agents include, but are not limited to, rosin natural products such as abietic acid, dehydroabietic acid, pimaric acid, rosin soaps (such as the sodium salt of the rosin acids), hydrogenated derivatives of rosins and their alkyl ester derivatives made from glycerol or pentaerythritol or other such branched alcohols, non-ionic surfactants including long-chain or branched hydrocarbon alcohols, such as for example 2-ethylhexanol, lauryl alcohol, and stearyl alcohol, and alcohol ethoxylates; acrylic-based polymers such as poly(acrylic acid), poly(methyl methacrylate), styrene-based copolymers such as poly(styrene sodio-sulfonate) and poly(styrene)-co-poly(alkyl (meth)acrylate), copolymers of α-olefins such as 1-hexadecene, 1-octadecene, 1-eicosene, 1-triacontene and the like, copolymers of 4-vinyl pyridine, vinyl imidazole, and vinyl pyrrolidinone, polyester copolymers, polyamide copolymers, copolymers of acetals and acetates, such as the copolymer poly(vinylbutyral)-co-(vinyl alcohol)-co-(vinyl acetate).

The types of non-covalent chemical bonding that can occur between the precursor/pigment and the stabilizer are, for example, van der Waals' forces, ionic or coordination bonding, hydrogen bonding, and/or aromatic pi-stacking bonding. In embodiments, the non-covalent bonding is predominately hydrogen bonding and van der Waals' forces, but can include aromatic pi-stacking bonding as additional or alternative types of non-covalent bonding between the stabilizer compounds and the precursor/pigment.

The "average" pigment particle size, which is typically represented as $d_{50}$, is defined as the median particle size value at the 50th percentile of the particle size distribution, wherein 50% of the particles in the distribution are greater than the $d_{50}$ particle size value and the other 50% of the particles in the distribution are less than the $d_{50}$ value. Average particle size can be measured by methods that use light scattering technology to infer particle size, such as Dynamic Light Scattering. The term "particle diameter" as used herein refers to the length of the pigment particle at the longest dimension (in the case of acicular shaped particles) as derived from images of the particles generated by Transmission Electron Microscopy (TEM). The term "nano-sized", "nanoscale", "nanoscopic", or "nano-sized pigment particles" refers to for instance, an average particle size, $d_{50}$, or an average particle diameter of less than about 150 nm, such as of about 1 nm to about 100 nm, or about 10 nm to about 80 nm. Geometric standard deviation is a dimensionless number that typically estimates a population's dispersion of a given attribute (for instance, particle size) about the median value of the population and is derived from the exponentiated value of the standard deviation of the log-transformed values. If the geometric mean (or median) of a set of numbers $\{A1, A2, \ldots, A_n\}$ is denoted as $\mu_g$, then the geometric standard deviation is calculated as:

$$\sigma_g = \exp\sqrt{\frac{\sum_{i=1}^{n}(\ln A_i - \ln \mu_g)^2}{n}}$$

The method of making nano-sized particles of the benzimidazolone pigments such as those described above is a process that involves at least one or more reaction steps. A diazotization reaction is a key reaction step for synthesis of the monoazo laked pigment, whereby a suitably substituted aromatic amine is either directly or indirectly converted first to a diazonium salt using standard procedures, such as that which includes treatment with an effective diazotizing agent such as nitrous acid $HNO_2$ (which is generated in situ by mixing sodium nitrite with dilute protic acid solution such as hydrochloric acid), or nitrosyl sulfuric acid (NSA), which is commercially available or can be prepared by mixing sodium nitrite in concentrated sulfuric acid. The diazotization procedure is typically carried out at cold temperatures so as to keep the diazonium salt stable, but in some cases may be carried out at room temperature. The resulting reaction mixture will comprise mainly the diazonium salt either dissolved or as a finely suspended solid in acidic medium.

A second solution or suspension is prepared by dissolving or suspending the benzimidazolone coupling component mainly into water, which may optionally contain another liquid such as an organic solvent (for example, iso-propanol, tetrahydrofuran, methanol, N-methyl-2-pyrrolidone, N,N-dimethylacetamide, dimethylsulfoxide, or other). The second solution also contain either acids or bases and buffers to render the benzimidazolone coupler component into either an aqueous solution or a fine particle suspension and to aid reaction with the diazonium salt solution. Suitable acids, bases and buffers include, for example, sodium or potassium hydroxide, acetic acid, and sodium acetate. The second solution additionally contains any surface active agents, and includes the sterically bulky stabilizer compounds such as those described previously. This second mixture is charged within a larger vessel in order to carry out the desired coupling reaction with the diazonium salt solution.

In further embodiments, the benzimidazolone coupling component can be provided either already prepared, or it can be prepared from suitable precursor materials prior to being formed into the indicated second solution. Where the benzimidazolone coupler component is prepared from suitable precursor materials, the suitable precursor materials can be any materials that when reacted appropriately will provide the desired benzimidazolone coupler component. For example, many benzimidazolone coupler components can be prepared from 5-amino-benzimidazolone:

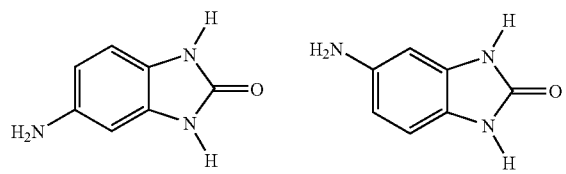

as a starting material. The 5-amino-benzimidazolone can then be reacted with suitable materials to provide the benzimidazolone coupler component.

The first reaction mixture containing the dissolved or suspended diazonium salt is then transferred into the second solution or suspension of the desired benzimidazolone coupler component, and the temperature of the mixture can range from about 10° C. to about 75° C., in order to produce a solid colorant material suspended as a precipitate in an aqueous slurry, which is the desired benzimidazolone pigment product formed as nano-sized particles. There are several chemical as well as physical processing factors that can affect the final particle size, shape and distribution of the benzimidazolone pigment nanoparticles, including stoichiometries of the starting reactants, choice and loading of surface active agents and stabilizer compounds, the concentrations of chemical species in the liquid medium, pH of liquid medium, temperature, the order and the rate of reactant addition, agitation rate, post-reaction treatments such as heating, isolation and washing of particles, and drying conditions.

In embodiments, the slurry of pigment nanoparticles is not treated nor processed any further, such as performing additional heating, but instead is isolated immediately by vacuum filtration or centrifugal separation processes. The pigment solids can be washed copiously with deionized water to remove excess salts or additives that are not tightly associated or bonded with the pigment particle surface. The pigment solids are dried by freeze-drying under high vacuum, or alternatively, by vacuum-oven drying. The resulting pigment consists of predominantly nano-sized primary particles and particle aggregates that are loosely agglomerated and of high quality, which when imaged by TEM (Transmission Electron Microscopy), exhibit primary pigment particles and small aggregates ranging in diameters from about 20 nm to about 200 nm, and predominantly from about 50 nm to about 125 nm. (Here, it is noted that average particle size $d_{50}$ and particle size distributions are measured by Dynamic Light Scattering, an optical measurement technique that estimates the hydrodynamic radius of non-spherical pigment particles gyrating and translating in a liquid dispersion via Brownian motion, by measuring the intensity of the incident light scattered from the moving particles. As such, the $d_{50}$ particle size metric obtained by DLS technique is always a larger number than the actual particle diameters observed by TEM imaging.)

Pigment particles of benzimidazolone pigments such as Pigment Yellow 151 and Pigment Red 175 that have smaller particle sizes could also be prepared by the above method in the absence of using sterically bulky stabilizers and with the use of surface active agents alone (for example, only rosin-type surface agents), depending on the concentrations and process conditions employed, but the pigment product will not predominantly exhibit nano-sized particles nor will the particles exhibit regular morphologies. In the absence of using the sterically bulky stabilizer compound, the methods described above typically produce larger, rod-like particle aggregates, ranging in average particle diameter from 200-700 nm and with wide particle distribution and (length:width) aspect ratio, and such particles are difficult to either wet and/or disperse into a coating matrix and generally give poor coloristic properties. In embodiments, the combined use of a suitable sterically bulky stabilizer compound with optionally a minor amount of suitable surface active agent, such as rosin-type surfactants or alcohol ethoxylates, using the synthesis methods described previously would afford the smallest fine pigment particles having nanometer-scale diameters, more narrow particle size distribution, and low aspect ratio. Various combinations of these compounds, in addition to variations with process parameters such as stoichiometry of reactants, concentration, addition rate, temperature, agitation rate, reaction time, and post-reaction product recovery processes, enables the formation of pigment particles with tunable average particle size ($d_{50}$) from nanoscale sizes (about 1 to about 100 nm) to mesoscale sizes (about 100 to about 500 nm) or larger.

The advantages of this process include the ability to tune particle size and composition for the intended end-use application of the benzimidazolone pigment, such as toners and inks and coatings, which include phase-change, gel-based and radiation-curable inks, solid and non-polar liquid inks, solvent-based inks and aqueous inks and ink dispersions. For the end-use application in piezoelectric inkjet printing, nano-sized particles are advantageous to ensure reliable inkjet printing and prevent blockage of jets due to pigment particle agglomeration. In addition, nano-sized pigment particles are advantageous for offering enhanced color properties in printed images.

In embodiments, the nano-sized pigment particles that were obtained for benzimidazolone pigments can range in the average particle size, $d_{50}$, or in the average particle diameter, from about 10 nm to about 250 nm, such as from about 25 nm to about 175 nm, or from about 50 nm to about 150 nm, as measured by either dynamic light scattering method or from TEM images. The shape of the nano-sized pigment particles can be one or more of several morphologies, including rods, platelets, needles, prisms or nearly spherical, and the aspect ratio of the nanosize pigment particles can range from 1:1 to about 10:1, such as having aspect ratio between 1:1 and 5:1; however the actual metric can lie outside of these ranges.

The formed nanoscale pigment particle compositions can be used, for example, as coloring agents in a variety of compositions, such as in liquid (aqueous or non-aqueous) ink vehicles, including inks used in conventional pens, markers, and the like, liquid ink jet ink compositions, solid or phase change ink compositions, and the like. For example, the colored nanoparticles can be formulated into a variety of ink vehicles, including "low energy" solid inks with melt temperatures of about 60 to about 130° C., solvent-based liquid inks or radiation-curable such as UV-curable liquid inks comprised of alkyloxylated monomers, and even aqueous inks.

In addition to ink compositions, the nanoscale benzimidazolone pigment particle compositions can be used in a variety of other applications, where it is desired to provide a specific color to the composition. For example, the compositions can also be used in the same manner as conventional pigments in such uses as colorants for paints, resins, lenses, filters, printing inks, and the like according to applications thereof. By way of example only, the compositions of embodiments can be used for toner compositions, which include polymer particles and nanoscale pigment particles, along with other optional additives, that are formed into toner particles and optionally treated with internal or external additives such as flow aids, charge control agents, charge-enhancing agents, filler particles, radiation-curable agents or particles, surface release agents, and the like. The toner composition of the present invention can be prepared by a number of known methods including extrusion melt blending of the toner resin particles, nanoscale pigment particles and other colorants and other optional additives, followed by mechanical commination and classification. Other methods include those well known in the art such as spray drying, melt dispersion, extrusion processing, dispersion polymerization, and suspension polymerization. Further, the toner compositions can be prepared by emulsion/aggregation/coalescence processes, as disclosed in references U.S. Pat. No. 5,290,654, U.S. Pat. No. 5,278,020, U.S. Pat. No. 5,308,734, U.S. Pat. No. 5,370,963, U.S. Pat. No. 5,344,738, U.S. Pat. No. 5,403,693, U.S. Pat. No. 5,418,108, U.S. Pat. No. 5,364,729, and U.S. Pat. No. 5,346,797. The toner particles can in turn be mixed with carrier particles to form developer compositions. The toner and developer compositions can be used in a variety of electrophotographic printing systems.

Examples are set forth herein below and are illustrative of different compositions and conditions that can be utilized in practicing the disclosure. All proportions are by weight unless otherwise indicated. It will be apparent, however, that the disclosure can be practiced with many types of compositions and can have many different uses in accordance with the disclosure above and as pointed out hereinafter.

EXAMPLES

Comparative Example 1

Synthesis of Pigment Yellow 151 (No Steric Stabilizer, No Surfactant)

Into a 250 mL round bottom flask is charged anthranilic acid (6.0 g, available from Sigma-Aldrich, Milwaukee, Wis.), deionized water (80 mL) and 5M HCl aqueous solution (20 mL). The mixture is stirred at room temperature until all solids are dissolved, then cooled to 0° C. A solution of sodium nitrite (3.2 g) is dissolved in deionized water (8 mL) and then is added dropwise into the solution of anthranilic acid at a rate that maintains the internal temperature range in the mixture of 0-5° C. Once diazotization is complete, the solution is stirred an additional 0.5 hr. Prior to coupling reaction, any excess nitrite ion is destroyed using aliquots of dilute aqueous urea solution. A second mixture for the coupling component is prepared by charging deionized water (100 mL) and sodium hydroxide (5.5 g) into a 500-mL vessel, stirring to dissolution, then adding 5-(acetoacetamido)-2-benzimidazolone (10.5 g, available from TCI America, Portland, Oreg.) into this solution while vigorously stirring until all solids dissolved. A separate solution containing glacial acetic acid (15 mL), 5M NaOH solution (30 mL) and deionized water (200 mL) is then added dropwise into the alkaline solution of coupling component while stirring vigorously, after which the coupling component is precipitated as a white suspension of particles, and the mixture is weakly acidic. For coupling reaction, the chilled diazotization mixture is slowly added dropwise into the suspension of coupling component, while stirring vigorously, to produce a reddish-yellow slurry of pigment. The slurry is stirred at room temperature for another 2 hours, after which time the pigment is isolated by vacuum-filtration, is washed with several volumes of deionized water (3 portions of 250 mL), then freeze-dried. Reddish-yellow granules of pigment are obtained, and TEM images show large aggregates of rod-shaped particles having high aspect ratio, with particle diameters ranging from 200 to 500 mm.

Comparative Example 2

Synthesis of Pigment Yellow 151 (in Presence of 2-Ethylhexanol Surfactant)

Into a 250 mL round bottom flask is charged anthranilic acid (3.0 g, available from Sigma-Aldrich, Milwaukee, Wis.), deionized water (40 mL) and 5M HCl aqueous solution (10 mL). The mixture is stirred at room temperature until all solids are dissolved, then cooled to 0° C. A solution of sodium nitrite (1.6 g) is dissolved in deionized water (5 mL) and then is added dropwise into the solution of anthranilic acid at a rate that maintains the internal temperature range in the mixture of 0-5° C. Once diazotization is complete, the solution is stirred an additional 0.5 hr. Prior to the coupling reaction, any excess nitrite ion is destroyed using aliquots of dilute aqueous urea solution. A second mixture for the coupling component is prepared by charging deionized water (40 mL) and sodium hydroxide (2.8 g) into a 250-mL vessel, stirring to dissolution, then adding 5-(acetoacetamido)-2-benzimidazolone (5.25 g, available from TCI America, Portland, Oreg.) into this solution while vigorously stirring, followed after by adding 2-ethylhexanol as surfactant (4 mL, available from Sigma-Aldrich, Milwaukee, Wis.), stirring until all solids dissolved. A separate solution containing glacial acetic acid (7.5 mL), 5M NaOH solution (15 mL) and deionized water (80 mL) is then added dropwise into the alkaline solution of coupling component while stirring vigorously, after which the coupling component is precipitated as a white suspension of particles, and the mixture is weakly acidic. The cold diazotization mixture is slowly added dropwise into the suspension of coupling component, while stirring vigorously, to produce a dark yellow slurry of pigment solids, whichs is stirred at room temperature for another 2 hours, after which time the pigment is a lighter yellow color. The pigment solids are collected by vacuum-filtration, rinsing with three volumes of deionized water (200 mL each), then methanol (50 mL), and a final rinse with deionized water (50 mL), and lastly is freeze-dried. Bright yellow granules of pigment are obtained, and TEM images show aggregates of smaller rod-shaped particles, with particle diameters ranging from about 75 nm to about 250 nm.

Example 1

Synthesis of Nano-Sized Particles of Pigment Yellow 151 (with Stearyl Amide as Steric Stabilizer)

Into a 250 mL round bottom flask is charged anthranilic acid (3.0 g, available from Sigma-Aldrich, Milwaukee, Wis.), deionized water (40 mL) and 5M HCl aqueous solution (10 mL). The mixture is stirred at room temperature until all solids are dissolved, then cooled to 0° C. A solution of sodium nitrite (1.6 g) is dissolved in deionized water (5 mL) and then is added dropwise into the solution of anthranilic acid at a rate that maintains the internal temperature range in the mixture of 0-5° C. Once diazotization is complete, the solution is stirred an additional 0.5 hr. Prior to the coupling reaction, any excess nitrite ion is destroyed using aliquots of dilute aqueous urea solution. A second mixture for the coupling component is prepared by charging deionized water (30 mL) and sodium hydroxide (2.8 g) into a 250-mL vessel, stirring to dissolution, then adding 5-(acetoacetamido)-2-benzimidazolone (5.25 g, available from TCI America, Portland, Oreg.) into this solution while vigorously stirring. A warm solution of stearamide (1.6 g, available from Sigma-Aldrich, Milwaukee, Wis.) dissolved in tetrahydrofuran (20 mL) is added into the mixture. A separate solution containing glacial acetic acid (7.5 mL), 5M NaOH solution (15 mL) and deionized water (80 mL) is then added dropwise into the alkaline solution of coupling component while stirring vigorously, after which the coupling component is precipitated as a suspension of white particles and is weakly acidic. The cold diazotization mixture is slowly added dropwise into the suspension of coupling component, while stirring vigorously, to produce a dark yellow slurry of pigment solids, whichs is stirred at room temperature for another 2 hours, after which time the pigment is a lighter yellow color. The pigment solids are collected by vacuum-filtration through a membrane cloth having small pore size (800 nm or smaller), rinsing with three volumes of deionized water (200 mL each), then methanol (50 mL), and a final rinse with deionized water (50 mL), and lastly is freeze-dried. Bright yellow granules of pigment are obtained, and TEM images show aggregates of small rod-shaped particles having low aspect ratio, with particle diameters ranging from about 40 nm to about 150 nm, with the majority of particles having long diameters of less than about 100 nm.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A nanoscale pigment particle composition, comprising:
   a benzimidazolone pigment, and
   a sterically bulky stabilizer compound associated non-covalently with the benzimidazolone pigment;
   wherein presence of the stabilizer limits an extent of particle growth and aggregation, to afford nanoscale-sized pigment particles.

2. The composition of claim 1, wherein the nanoscale-sized pigment particles have an average particle diameter as derived from transmission electron microscopy imaging, of less than about 150 nm.

3. The composition of claim 1, wherein the benzimidazolone pigment comprises a diazo component group and a nucleophilic coupling component group that are linked together with one azo group, wherein at least one of the diazo component group and the nucleophilic coupling component group comprises a benzimidazolone functional moiety.

4. The composition of claim 3, wherein the diazo component group is selected from the group consisting of $DC_1$ to $DC_5$:

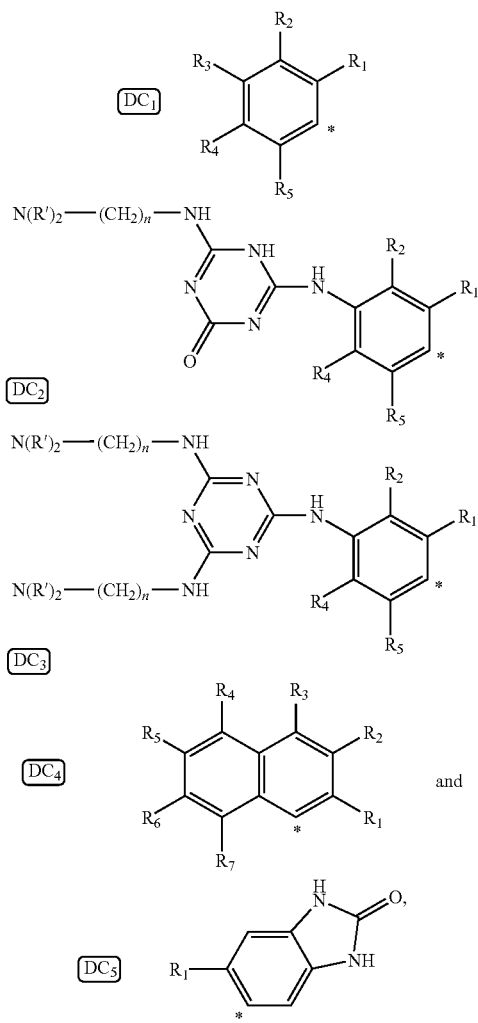

wherein:
* indicates the point of attachment to the azo group in the benzimidazolone pigment,
$R_1$ to $R_7$ independently represent H; $CH_3$; $CO_2H$; $CO_2CH_3$; $CO_2(CH_2)_nCH_3$ wherein n=0-5; $CONH_2$; $(CO)R_aR_b$ wherein $R_a$ and $R_b$ can independently represent H, $C_6H_5$, $(CH_2)_nCH_3$ wherein n=0-12, or $(CH_2)_nN(CH_3)_2$ wherein n=1-5; $OCH_3$; $OCH_2CH_2OH$; $NO_2$; $SO_3H$; Cl; Br; I; F; or any of the following structural groups:

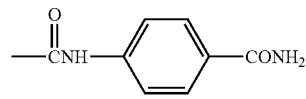

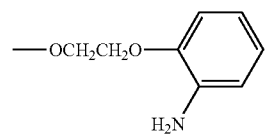

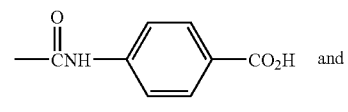

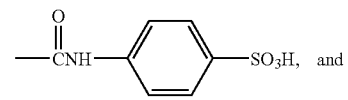

in $DC_2$ and $DC_3$ R' represents H, $(CH_2)_nCH_3$, or $C_6H_5$, and n represents a number of from 1 to about 6.

5. The composition of claim 3, wherein the nucleophilic coupling component group is selected from the group consisting of:

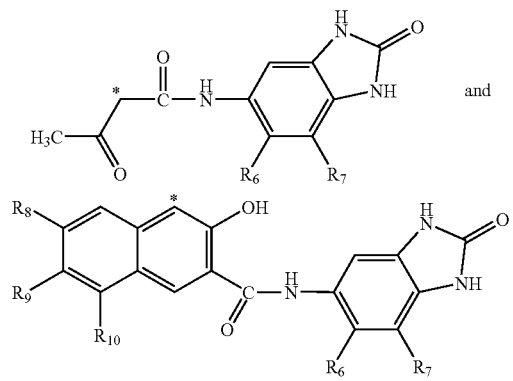

wherein $R_6$, $R_7$, $R_8$, $R_9$, and $R_{10}$ independently represent H, Br, Cl, I, F, or $CH_3$, and * denotes the point of attachment to the azo group.

6. The composition of claim 1, wherein the sterically bulky stabilizer is associated with the benzimidazolone pigment predominantly by hydrogen bonding.

7. The composition of claim 1, wherein the sterically bulky stabilizer comprises at least one aliphatic hydrocarbon moiety.

8. The composition of claim 1, wherein the sterically bulky stabilizer is selected from the group consisting of mono- and di-carboxylic acids; mono- and di-esters; mono- and di-primary amide derivatives of pyridine, piperidine, piperazine, morpholine and pyrroles; monosubstituted pyridine, piperazine, piperidine, morpholine, pyrrole, imidazole, and thiazole, and cationic salts thereof, substituted by a long-chain or branched aliphatic hydrocarbon; poly(vinyl pyrrolidone) and copolymers of poly(vinyl pyrrolidone) with α-olefins; poly(vinyl imidazole) and copolymers of poly(vinyl imidazole) with α-olefins; poly(vinyl pyridine) and copolymers of poly(vinyl pyridine) with α-olefins or styrene; long-chain or branched aliphatic primary amides and amidines; semicarbazides and hydrazones of long-chain aliphatic and/or branched aldehydes and ketones; mono-substituted ureas and N-alkyl-N-methyl ureas, substituted by a long-chain or branched aliphatic hydrocarbon; mono-substituted monosubstituted guanidines and guanidinium salts, substituted by a long-chain or branched aliphatic hydrocarbon; mono- and di-substituted succinimides; mono- and di-substituted succinic acids or their esters, comprising one or more alkyl substituent comprised of a long-chain or branched aliphatic hydrocarbon having between 6 and 50 carbon atoms; and mixtures thereof.

9. The composition of claim 1, wherein the sterically bulky stabilizer is selected from the group consisting of the following compounds:

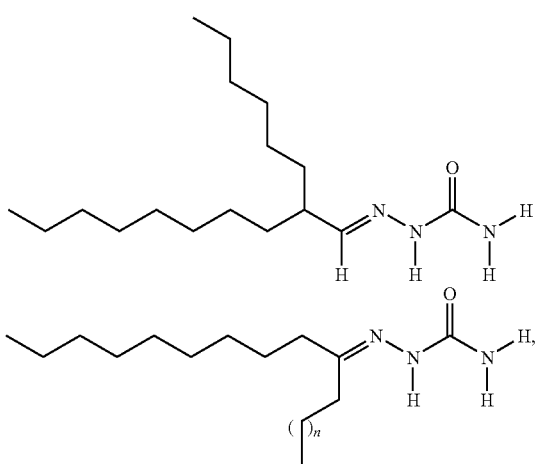

wherein m is an integer of 0 to 12, and R is H, CH$_3$, or (CH$_2$)$_n$CH$_3$ where n is an integer of 0 to 6,

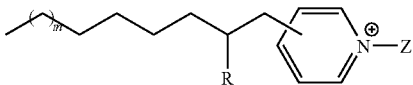

where m is an integer of 0 to 12, R is H or CH$_3$, and Z is Cl, Br, I, SO$_4^{2-}$, MeSO$_4^-$, or O$_3$S-p-(C$_6$H$_4$)CH$_3$,

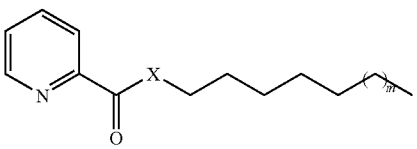

where m is an integer of 0 to 12, and X is O, NH, or S,

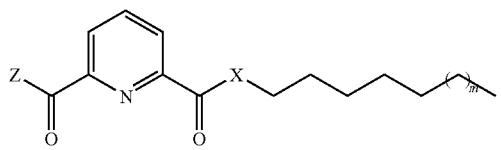

where m is an integer of 0 to 12, X is O, NH, or S, and Z is OH, NH$_2$, H, or CH$_3$,

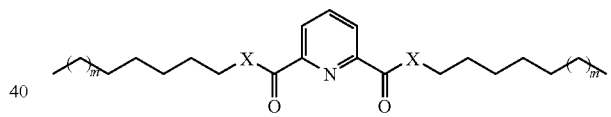

where each m is an integer of 0 to 12, and each X is O, NH, or S, where n is an integer of 0 to 10,

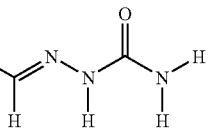

where n is an integer of 0 to 25,

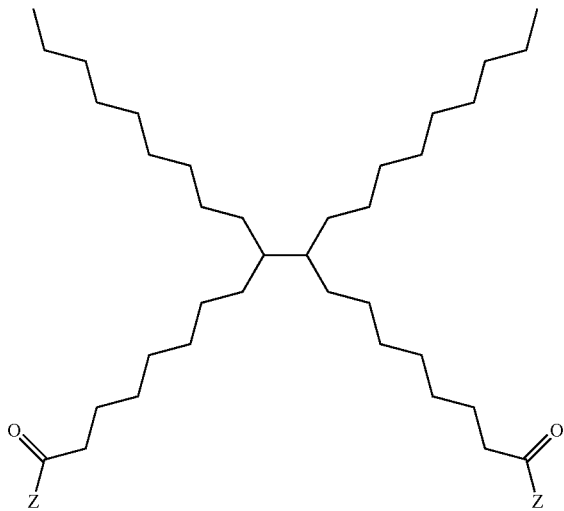

where each Z is H, OH, $NH_2$, NHR', or OR', where R' is $C_1$-$C_6$ alkyl or $C_6$-$C_{14}$ aryl group,

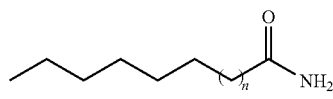

where n is an integer of 1 to 30,

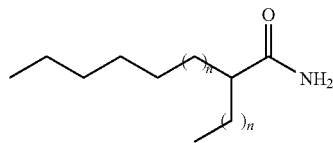

where m is an integer of 1 to 30, and n is an integer of 1 to 11,

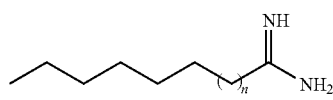

where n is an integer of 1 to 30,

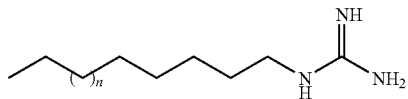

where n is an integer of 1 to 14, and

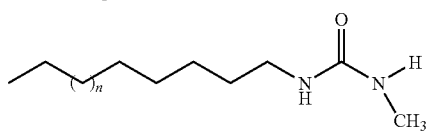

where n is an integer of 1 to 30.

10. The composition of claim 1, further comprising a surfactant selected from the group consisting of derivatives of rosin natural products; long-chain or branched hydrocarbon alcohols; alcohol ethoxylates; acrylic-based polymers; styrene-based copolymers; copolymers of α-olefins; copolymers of vinyl pyridine, vinyl imidazole, and vinyl pyrrolidinone; polyester copolymers; polyamide copolymers; and copolymers of acetals and acetates.

11. A process for preparing nanoscale particles of benzimidazolone pigments, comprising:
providing one or more organic pigment precursors to a benzimidazolone pigment comprising a benzimidazolone moiety,
providing a solution or suspension of a sterically bulky stabilizer compound that associates non-covalently with the benzimidazolone moiety on one of the pigment precursors, and
carrying out a chemical coupling reaction to form a benzimidazolone pigment composition comprising nanoscale-sized pigment particles, whereby the pigment precursors are incorporated with the benzimidazolone pigment and one or more functional moieties on the benzimidazolone pigment is non-covalently associated with the steric stabilizer, so as to limit an extent of particle growth and aggregation.

12. The process of claim 11, wherein the nanoscale-sized pigment particles have an average particle diameter as derived from transmission electron microscopy imaging, of less than about 150 nm.

13. The process of claim 11, further comprising adding a surfactant selected from the group consisting of rosin compounds; long-chain or branched hydrocarbon alcohols; alcohol ethoxylates; acrylic-based polymers; styrene-based copolymers; copolymers of α-olefins; copolymers of vinyl pyridine, vinyl imidazole, and vinyl pyrrolidinone; polyester copolymers; polyamide copolymers; and copolymers of acetals and acetates.

14. The process of claim 11, wherein the non-covalent association between the benzimidazolone pigment and the sterically bulky stabilizer compound is predominantly hydrogen bonding.

15. The process of claim 11, comprising:
preparing a first reaction mixture comprising: (a) a diazonium salt as a first precursor to the benzimidazolone pigment and (b) a liquid medium containing diazotizing agents in acid solution or suspension; and
preparing a second reaction mixture comprising: (a) a benzimidazolone coupling agent as a second precursor to the benzimidazolone pigment and (b) a sterically bulky stabilizer compound that can associate non-covalently with the coupling agent; and (c) a liquid medium
combining the first reaction mixture into the second reaction mixture to form a third mixture and
effecting a direct coupling reaction which forms a benzimidazolone pigment composition having nanoscale-sized particles and wherein the benzimidazolone pigment associates non-covalently with the sterically bulky stabilizer.

16. The process of claim 15, wherein the second reaction mixture further comprises one or more additives selected from the group consisting of inorganic and organic buffers, alkaline bases, and acids.

17. The process of claim 15, wherein the combining is conducted at ambient temperature with stirring.

18. The process of claim 15, wherein the benzimidazolone pigment comprises a diazo component group and a nucleophilic coupling component group that are linked together with one azo group, wherein at least one of the diazo component group and the nucleophilic coupling component group comprises a benzimidazolone functional moiety.

19. The process of claim 18, wherein the diazo component group is selected from the group consisting of $DC_1$ to $DC_5$:

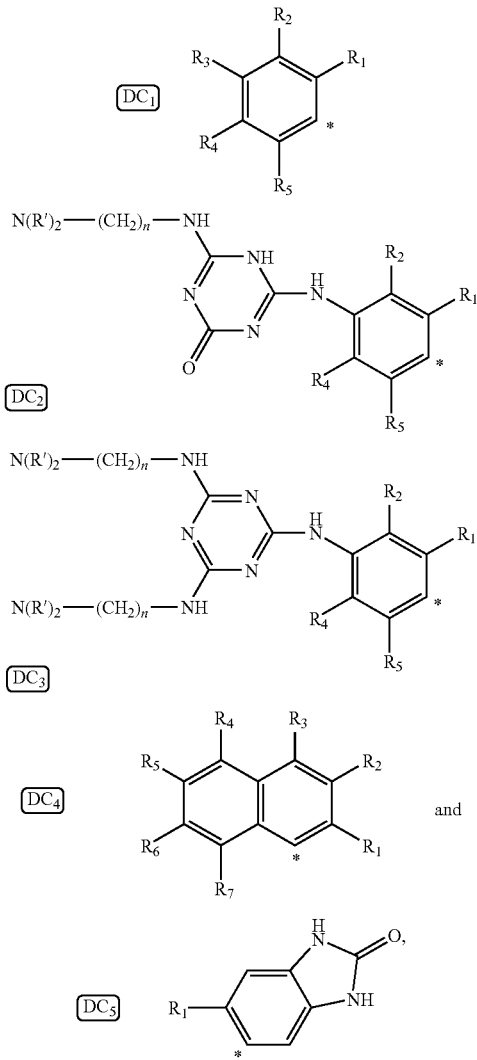

wherein:
* indicates the point of attachment to the azo group in the benzimidazolone pigment,
$R_1$ to $R_7$ independently represent H; $CH_3$; $CO_2H$; $CO_2CH_3$; $CO_2(CH_2)_nCH_3$ wherein n=0-5; $CONH_2$; $(CO)R_aR_b$ wherein $R_a$ and $R_b$ can independently represent H, $C_6H_5$, $(CH_2)_nCH_3$ wherein n=0-12, or $(CH_2)_nN(CH_3)_2$ wherein n=1-5; $OCH_3$; $OCH_2CH_2OH$; $NO_2$; $SO_3H$; Cl; Br; I; F; or any of the following structural groups:

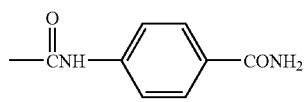

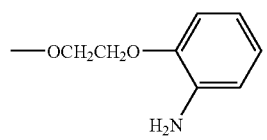

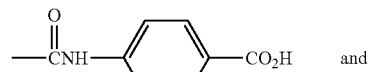

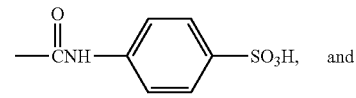

in $DC_2$ and $DC_3$ R' represents H, $(CH_2)_nCH_3$, or $C_6H_5$, and n represents a number of from 1 to about 6.

20. The process of claim 18, wherein the nucleophilic coupling component group is selected from the group consisting of:

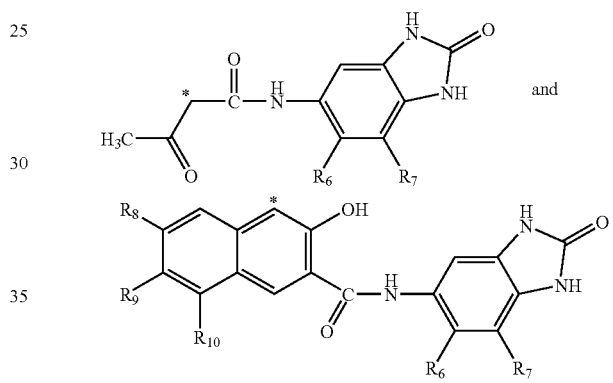

wherein $R_6$, $R_7$, $R_8$, $R_9$, and $R_{10}$ independently represent H, Br, Cl, I, F, or $CH_3$, and * denotes the point of attachment to the azo group.

21. The process of claim 15, wherein the sterically bulky stabilizer is selected from the group consisting of mono- and di-carboxylic acids; mono- and di-esters; mono- and di-primary amide derivatives of pyridine, piperidine, piperazine, morpholine and pyrroles; monosubstituted pyridine, piperazine, piperidine, morpholine, pyrrole, imidazole, and thiazole, and cationic salts thereof, substituted by a long-chain or branched aliphatic hydrocarbon; poly(vinyl pyrrolidone) and copolymers of poly(vinyl pyrrolidone) with α-olefins; poly(vinyl imidazole) and copolymers of poly(vinyl imidazole) with α-olefins; poly(vinyl pyridine) and copolymers of poly(vinyl pyridine) with α-olefins or styrene; long-chain or branched aliphatic primary amides and amidines; semicarbazides and hydrazones of long-chain aliphatic and/or branched aldehydes and ketones; mono-substituted ureas and N-alkyl-N-methyl ureas, substituted by a long-chain or branched aliphatic hydrocarbon; mono-substituted monosubstituted guanidines and guanidinium salts, substituted by a long-chain or branched aliphatic hydrocarbon; mono- and di-substituted succinimides; mono- and di-substituted succinic acids or their esters, comprising one or more alkyl substituent comprised of a long-chain or branched aliphatic hydrocarbon having between 6 and 50 carbon atoms; and mixtures thereof.

22. The process of claim 15, wherein the sterically bulky stabilizer is selected from the group consisting of the following compounds:

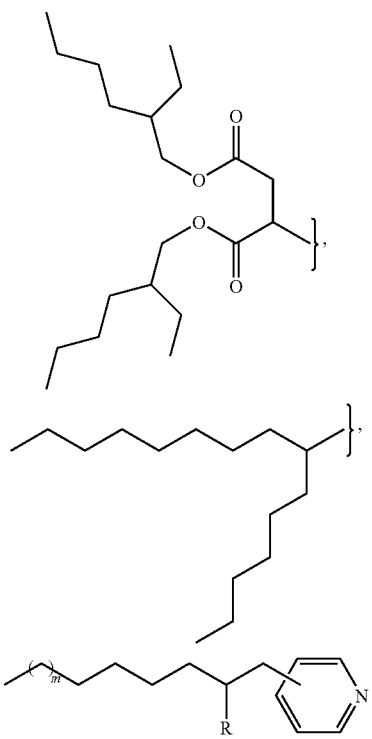

wherein m is an integer of 0 to 12, and R is H, CH$_3$, or (CH$_2$)$_n$CH$_3$ where n is an integer of 0 to 6,

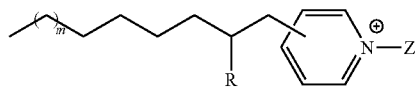

where m is an integer of 0 to 12, R is H or CH$_3$, and Z is Cl, Br, I, SO$_4^{2-}$, MeSO$_4^-$, or O$_3$S-p-(C$_6$H$_4$)CH$_3$,

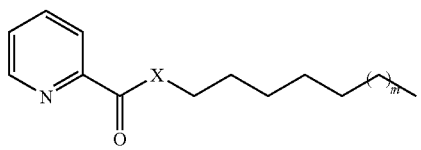

where m is an integer of 0 to 12, and X is O, NH, or S,

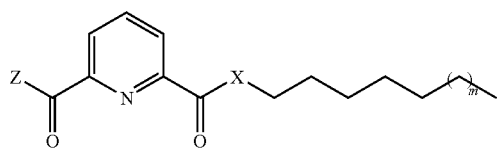

where m is an integer of 0 to 12, X is O, NH, or S, and Z is OH, NH$_2$, H, or CH$_3$,

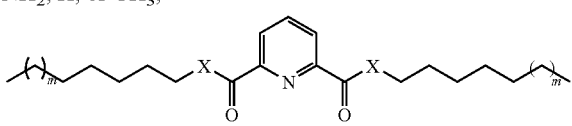

where each m is an integer of 0 to 12, and each X is O, NH, or S,

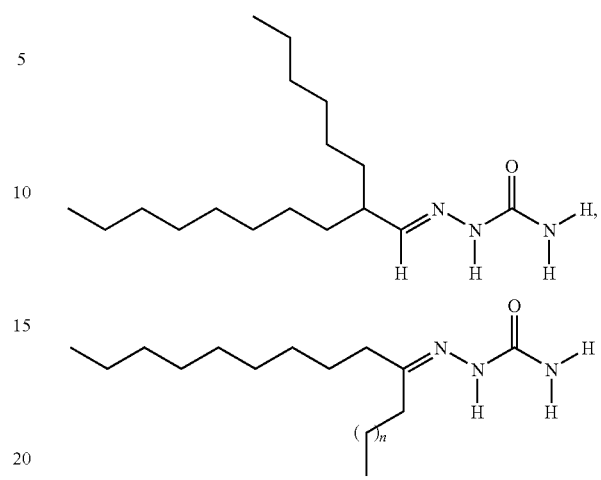

where n is an integer of 0 to 10,

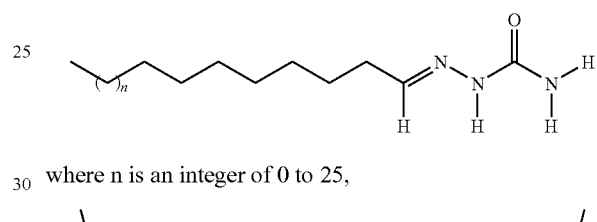

where n is an integer of 0 to 25,

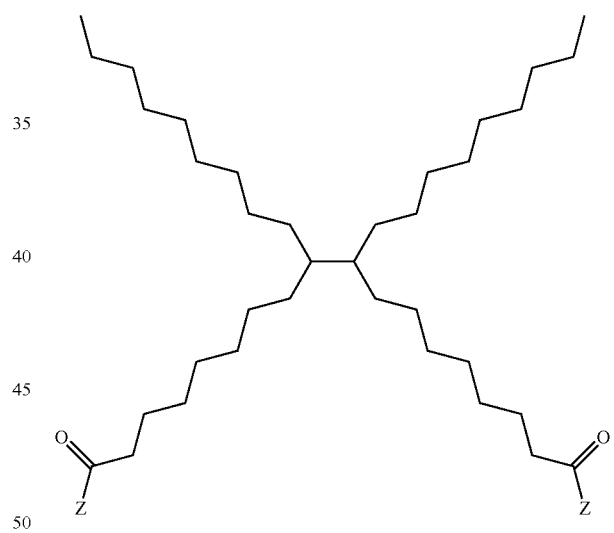

where each Z is H, OH, NH$_2$, NHR', or OR', where R' is C$_1$-C$_6$ alkyl or C$_6$-C$_{14}$ aryl group,

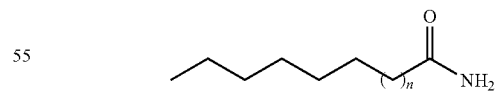

where n is an integer of 1 to 30,

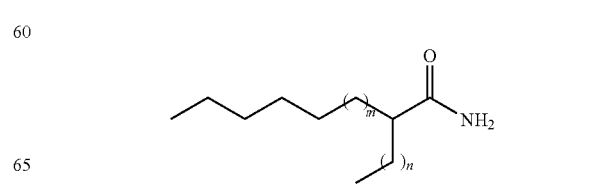

where m is an integer of 1 to 30, and n is an integer of 1 to 11,

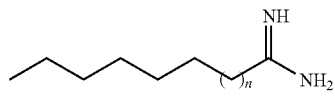

where n is an integer of 1 to 30,

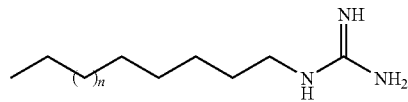

where n is an integer of 1 to 14, and

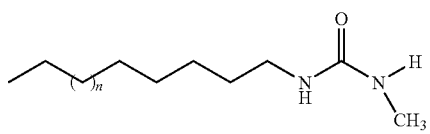

where n is an integer of 1 to 30.

23. An ink composition comprising:
   a carrier, and
   a colorant comprising a nanoscale pigment particle composition according to claim 1.

24. The ink composition of claim 23, wherein the ink composition is selected from the group consisting of solid ink compositions, phase change ink compositions, curable ink compositions, aqueous ink compositions, and non-aqueous ink compositions.

25. A toner composition comprising:
   a binder resin, and
   a colorant comprising a nanoscale pigment particle composition according to claim 1.

* * * * *